United States Patent
Hibner et al.

(10) Patent No.: US 7,066,893 B2
(45) Date of Patent: Jun. 27, 2006

(54) BIOPSY METHOD

(75) Inventors: John A. Hibner, Mason, OH (US); Elizabeth L. Sebern, Cincinnati, OH (US); Michael Piller, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 267 days.

(21) Appl. No.: 10/164,198

(22) Filed: Jun. 6, 2002

(65) Prior Publication Data

US 2003/0229293 A1 Dec. 11, 2003

(51) Int. Cl.
*A61B 10/00* (2006.01)

(52) U.S. Cl. .................. 600/566; 600/567; 600/568; 606/167; 606/171

(58) Field of Classification Search ........ 600/564–568; 606/167, 170, 180, 184, 185
See application file for complete search history.

(56) References Cited

U.S. PATENT DOCUMENTS

| | | | |
|---|---|---|---|
| 5,106,364 A * | 4/1992 | Hayafuji et al. ............... 604/22 |
| 5,526,822 A * | 6/1996 | Burbank et al. ............ 600/567 |
| 5,782,775 A | 7/1998 | Milliman et al. |
| 5,817,034 A | 10/1998 | Milliman et al. |
| 5,944,673 A | 8/1999 | Gregoire et al. |
| 5,964,716 A | 10/1999 | Gregoire et al. |
| 6,019,733 A | 2/2000 | Farascioni |
| 6,022,362 A | 2/2000 | Lee et al. |
| 6,036,657 A | 3/2000 | Milliman et al. |
| 6,086,544 A | 7/2000 | Hibner et al. |
| 6,485,436 B1 * | 11/2002 | Truckai et al. ............... 600/564 |
| 6,497,706 B1 * | 12/2002 | Burbank et al. ............... 606/45 |
| 6,712,773 B1 * | 3/2004 | Viola .......................... 600/564 |

FOREIGN PATENT DOCUMENTS

| WO | WO 99/13775 | 3/1999 |
|---|---|---|
| WO | WO 99/15079 | 4/1999 |
| WO | WO 99/44506 | 9/1999 |

OTHER PUBLICATIONS

U.S. Appl. No. 10/163,780, filed Jun. 6, 2002.

* cited by examiner

*Primary Examiner*—Max F. Hindenburg
*Assistant Examiner*—Jonathan Foreman

(57) ABSTRACT

A biopsy device having an insert and related method are disclosed. The insert permits a user to obtain a tissue sample surrounding a center core(s) of removed tissue. The additional tissue provides an effective evaluation of whether all the desired tissue has been excised and a determination of whether an acceptable margin of healthy tissue has been removed.

14 Claims, 7 Drawing Sheets

BIOPSY METHOD

FIELD OF THE INVENTION

The present invention relates generally to a biopsy process, and more particularly pertains to a perimeter cut biopsy process.

BACKGROUND OF THE INVENTION

U.S. Pat. No. 6,086,544 discloses a MAMMOTOME® brand of surgical biopsy device which is considered to be somewhat related to the present invention as the surgical biopsy device has a piercer having a piercer tube with a tissue receiving side port located on the side of the distal end of the piercer tube for receiving tissue to be excised from a surgical patient. A tissue sample is drawn through the side port with the assistance of a vacuum and a cutter is then actuated to sever the tissue sample. Accordingly, the side port can be utilized to take a rotationally oriented tissue sample from the tissue surrounding the surgical biopsy device by rotationally orienting the surgical biopsy device with respect to the surrounding tissue of the surgical patient.

There are two primary approaches to removing tissue from a breast. One approach removes the mass in one or two large pieces, and the other approach removes the mass in multiple pieces (minimum of three pieces).

Devices which may be suitable to remove the mass in a single piece are disclosed in U.S. Pat. Nos. 6,077,231, 6,165,137 and 6,213,957, and in U.S. Pat. No. 6,080,113.

Devices intended to remove a mass in a single piece can include one or more disadvantages. For instance, such devices can result in bleeding, and do not provide effective means (e.g. a vacuum to evacuate blood and other fluids from the site) to quickly and effectively manage bleeding as vessels are severed. Such devices may allow only a single cylinder of tissue to be excised from the breast. Moreover, due to the irregular morphology of most breast cancers, it is often difficult to fully encompass the lesion without utilizing an excessively large diameter cutter.

Such devices may be used to remove an excised cylinder of tissue, however the excised tissue sample may not be oriented rotationally with respect to the breast. Thus if additional tissue must be removed, there is no indication of the orientation of the additional tissue with respect to the breast. Such devices can also involve an excessive number of procedural steps, requiring in excess of forty procedural steps.

SUMMARY OF THE INVENTION

The present invention provides a method for obtaining tissue samples from the perimeter of a biopsy site. At least one initial core specimen of tissue is removed by displacing the core specimen through at least one sample port in the probe housing, axially translating a cutter from a recessed proximal position to a distal position in the probe housing to cut the core specimen of tissue, and removing the core tissue specimen from the probe housing. Then a perimeter shave insert is inserted within the probe housing, wherein the perimeter shave insert defines at least one perimeter specimen chamber. At least one perimeter specimen of tissue is removed from a perimeter of the cavity of the core tissue specimen, by aligning a perimeter specimen chamber in the insert with the sample port, displacing the perimeter specimen of tissue through the sample port into the perimeter specimen chamber, and actuating the cutter from its recessed proximal position to its distal position to cut a perimeter specimen of tissue in the specimen chamber.

In greater detail, tissue is pulled into the specimen chamber by coupling a vacuum source to the specimen chamber. A tissue retraction arm can be moved axially to stack previously-taken perimeter specimens of tissue in the probe housing in a location proximal to the specimen chamber, to allow multiple perimeter specimens to be stacked within the probe housing after they are cut. A specimen of tissue can be branded/cauterized to preserve the rotational orientation of the specimen of tissue relative the tissue cavity.

The insert, which can define a single specimen chamber, can be rotated to align the single specimen chamber with a sample port in the probe housing. Alternatively, the insert can define two specimen chambers, and the insert is rotated to align the two specimen chambers with one or more sample ports in the probe housing.

In one process, a first insert defines a single specimen chamber and is rotated to align the single specimen chamber with one or more sample ports of the probe housing to take a core tissue sample, after which the first insert is removed and a second perimeter insert which defines two perimeter specimens chambers is inserted into the probe housing. The two perimeter specimen chambers are then aligned with the two sample ports to take first and second perimeter tissue specimens. After the first and second perimeter tissue specimens have been taken, the probe housing and the second perimeter insert are rotated approximately 90 degrees, and third and fourth perimeter tissue specimens, are taken, such that the first, second, third and fourth perimeter tissue specimens provide specimens with a contiguous 360 degree margin around the core tissue specimen.

Although the disclosed embodiments of the present invention are for excision and removal of cancerous lesions from breast tissue, the disclosed embodiments should be considered as exemplary only, as the invention also has applicability to the excision and removal of other types of tissue from other types of soft tissue such as the liver and the lungs.

BRIEF DESCRIPTION OF THE DRAWINGS

The present invention for a perimeter cut biopsy probe may be more readily understood by one skilled in the art with reference being made to the following detailed description of several preferred embodiments thereof, taken in conjunction with the accompanying drawings wherein like elements are designated by identical reference numerals throughout the several views, and in which:

FIG. 1 is a top or plan view of the distal end of a probe which is employed by the perimeter cut biopsy device of the present invention without a perimeter shave insert positioned therein.

FIG. 2 is a top or plan view of the distal end of the probe with a perimeter shave insert pursuant to the present invention positioned and inserted therein in place of a knockout pin.

FIG. 3 is a side elevational view.

FIGS. 7, 8 and 8A show the contribution thereto of a perimeter shave insert pursuant to a first embodiment of the present invention.

FIG. 6 is a view of the distal end of the first embodiment of the probe outer housing, and illustrates an optional RF cutting/tunneling blade, vacuum openings, and a single sample notch port.

FIG. 7 is a view of the distal end of the probe wherein a first embodiment of a perimeter shave insert pursuant to the present invention and the cutter are visible through the sample notch port.

FIG. 8 is a longitudinal cross sectional view of the distal end of the probe of FIG. 7, and illustrates the perimeter shave insert in its distal-most position, with a specimen chamber being aligned with the sample notch port and the cutter being in a retracted position, wherein the perimeter shave insert is shown with a central, axially-extending vacuum port communicating through vacuum ports with the specimen chamber and the vacuum ports in the probe housing.

FIG. 8A is an axial cross sectional view of the probe of FIG. 8 taken along sectional arrows 8A—8A in FIG. 8.

FIG. 9 illustrates a second embodiment of a needle probe housing having an RF cutting tip and two sample notch ports.

FIG. 10 illustrates the probe housing of FIG. 9 having a core insert for removal of a core of tissue placed therein, and also shows a cutter positioned at the proximal ends of the ports.

FIG. 11 is a longitudinal cross sectional view of the probe of FIG. 10, and illustrates the core insert for removal of a core of tissue having a vacuum lumen and vacuum ports defined in its lower portion.

FIG. 11A is an axial cross sectional view of the probe of FIG. 11 taken along sectional arrows 11A—11A in FIG. 11.

FIGS. 12, 13 and 13A are respectively a perspective view, a longitudinal cross sectional view, and a radial cross sectional view, taken along sectional arrows 13A—13A in FIG. 13, of the second embodiment of the needle probe housing having two sample notch ports with a second embodiment of a perimeter shave insert positioned therein which defines two sample chambers.

DETAILED DESCRIPTION OF THE DRAWINGS

Figure 1:
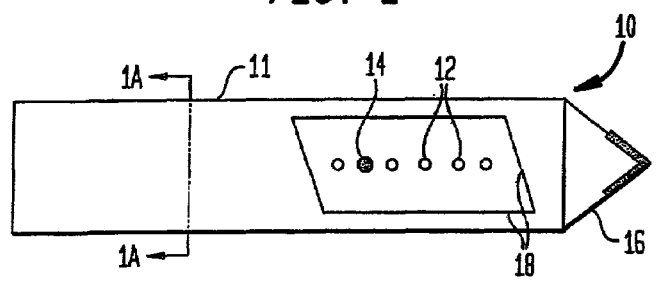
FIGS. 1, 2 and 3 are schematic illustrations of a simplified form of the present invention and show respectively, in FIG. 1 a perimeter cut biopsy needle probe housing, in FIG. 2 the needle probe housing of FIG. 1 having a perimeter shave insert inserted therein, and in FIG. 3 the needle probe housing having a perimeter shave insert positioned therein, wherein the specimen chamber of the insert is aligned with the sample port of the housing, and two already-removed perimeter specimens of tissue are temporarily stored in the proximal end of the probe housing.
Figure 2:
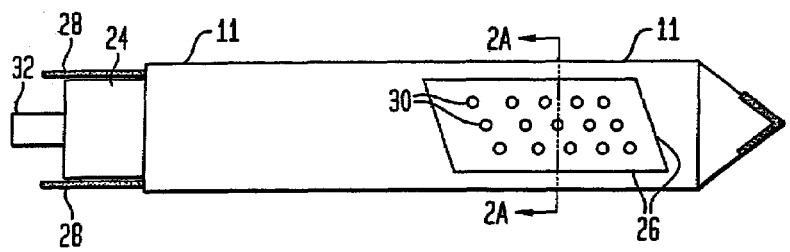
Figure 3:
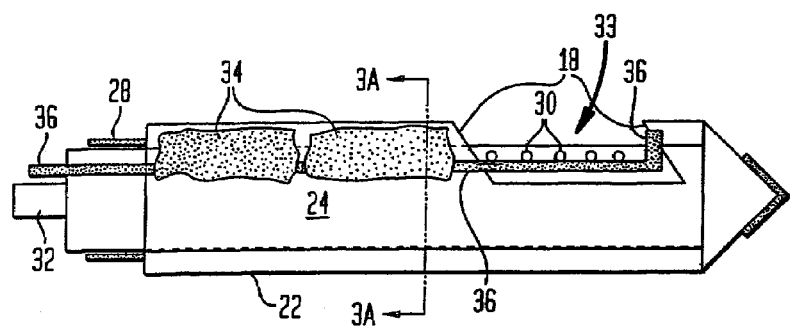

Referring to the drawings in detail, FIGS. 1, 2 and 3 are schematic illustrations of simplified forms of the present invention. FIG. 1 shows only a perimeter cut biopsy needle probe 10 having an outer housing 11. FIG. 2 illustrates the needle probe housing 11 of FIG. 1 having a perimeter shave insert 24 inserted therein. FIG. 3 shows the needle probe housing 11 having the perimeter shave insert 24 positioned therein with the specimen chamber 33 of the insert aligned with the sample port 18 of the housing, and two already-removed perimeter specimens of tissue 34 temporarily stored in the proximal end of the needle probe housing 11.

In greater detail, FIG. 1 is a side elevational view of the distal end of a probe 10 which is employed by the perimeter cut biopsy device of the present invention without a perimeter shave insert positioned therein. The distal end of the needle probe housing 11 includes vacuum openings 12, an optional tissue branding/cauterizing electrode 14, an RF cutting/tunneling tip 16, and a sample notch port 18.

Figure 1A:
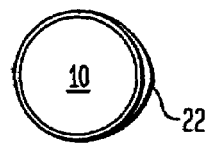
FIG. 1A is an axial sectional view of the probe of FIG. 1 taken along sectional arrows 1A—1A in FIG. 1, and illustrates a vacuum lumen mounted exterior to and on one side of the substantially round profile of the probe.

FIG. 1A is an axial sectional view of the probe of FIG. 1 taken along sectional arrows 1A—1A in FIG. 1, and illustrates an added vacuum lumen 22 mounted exterior to and on one side of the substantially round profile of the probe 10.

FIG. 2 is a side elevational plan view of the distal end of the probe with a perimeter shave insert 24 pursuant to the present invention positioned and inserted therein in place of a knockout pin/core insert usually positioned therein, wherein a perimeter specimen chamber 33 of the shave insert 24 extends to a sample notch port 26, and a cutter 28 is axially movable in the probe. Vacuum holes 30 are supplied with a vacuum by an axial vacuum source through an attachment 32, and/or a lateral vacuum source.

Figure 2A:
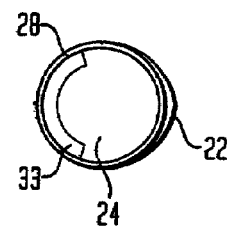
FIG. 2A is an axial sectional view of the probe of FIG. 2 taken along sectional arrows 2A—2A in FIG. 2, and illustrates the perimeter shave insert pursuant to the present invention and a specimen chamber defined therein.

FIG. 2A is an axial sectional view of the probe of FIG. 2 taken along sectional arrows 2A—2A in FIG. 2, and illustrates the perimeter shave insert 24 pursuant to the present invention which defines a specimen chamber 33 therein and the cutter 28 positioned in the probe for longitudinal movement therein.

Figure 3A:
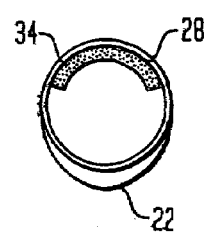
FIG. 3A is an axial sectional view of the probe of FIG. 3 taken along sectional arrows 3A—3A in FIG. 3, with the perimeter shave insert pursuant to the present invention having two preceding perimeter tissue slices positioned therein, and also shows the specimen chamber therein.

FIG. 3 is a side elevational view, and FIG. 3A is an axial sectional view of the probe of FIG. 3 taken along sectional arrows 3A—3A in FIG. 3, with the perimeter shave insert 24 pursuant to the present invention having two preceding perimeter tissue 34 positioned therein, a specimen chamber 33, and an optional tissue retraction arm 36 which is axially movable to stack the preceding tissue slices 34.

Figure 4:
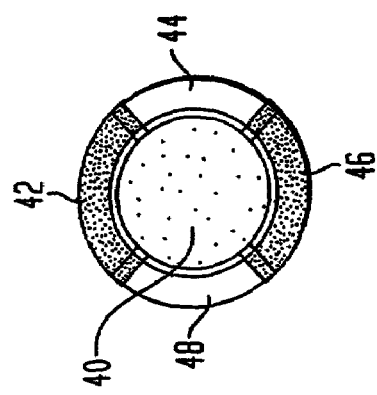
FIG. 4 is an axial sectional view of tissue specimens which have been taken by the probe, and shows a center core specimen, a 12 o'clock perimeter slice or shave, a 3 o'clock perimeter slice or shave, a 6 o'clock perimeter slice or shave, and a 9 o'clock perimeter slice or shave.

FIG. 4 is an axial sectional view of both center core and perimeter tissue specimens which have been taken by the probe, and show a center core specimen 40, a 12 o'clock perimeter slice or shave 42, a 3 o'clock perimeter slice or shave 44, a 6 o'clock perimeter slice or shave 46, and a 9 o'clock perimeter slice or shave 48.

Figure 5:
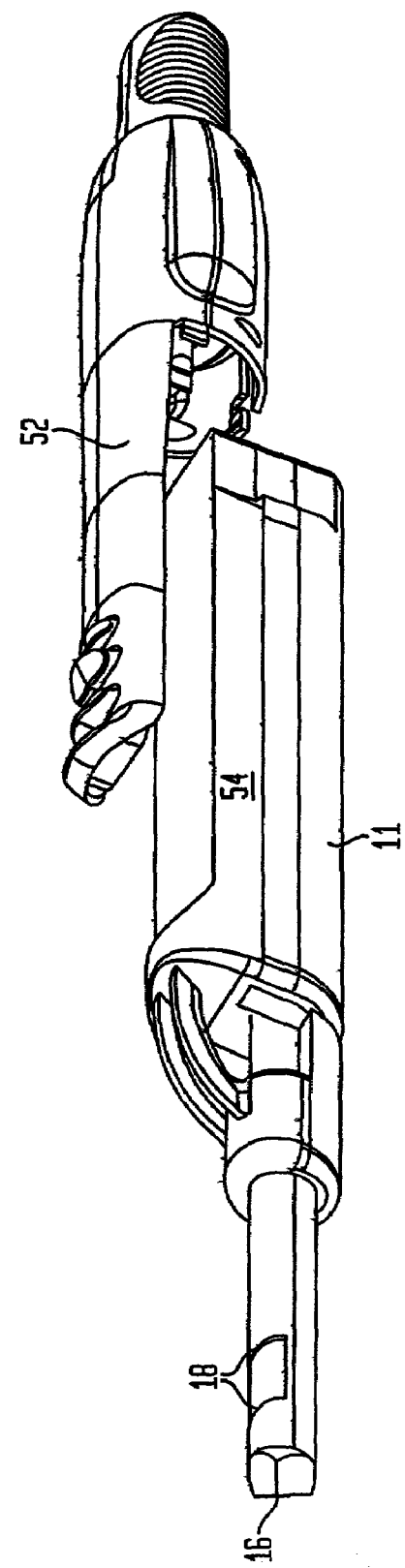
FIG. 5 is a front perspective view of one embodiment of a large gauge MAMMOTOME® perimeter cut biopsy probe of the prior art, which is used with the present invention, having a handpiece at a proximal end thereof and a probe tip at the distal end of the instrument, wherein the handpiece has been removed therefrom.

FIG. 5 is a front perspective view of one embodiment of a large gauge MAMMOTOME® perimeter cut biopsy probe of the prior art, which is also used with the present invention, having a probe housing 11, a handpiece 52 at a proximal end thereof, and a probe tip 16 at the distal end of the instrument, wherein the handpiece 52 has been removed therefrom.

Figure 6:
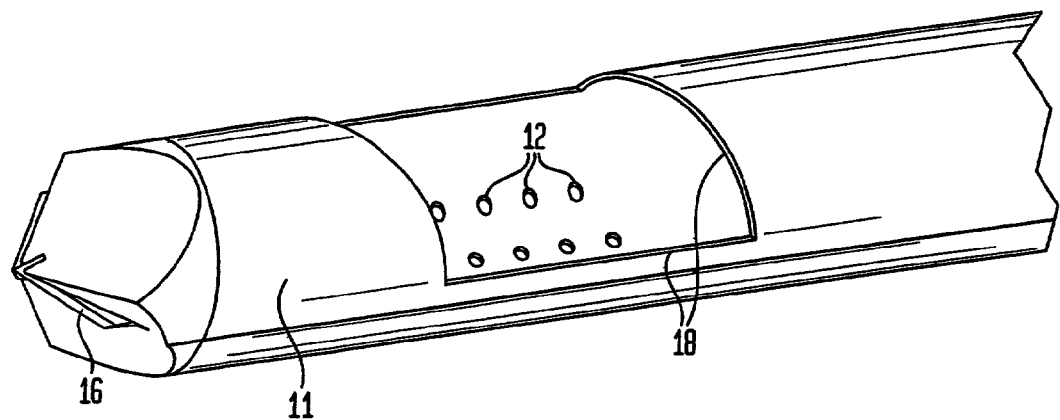
FIGS. 6, 7, 8 and 8A are respectively first and second perspective views, a longitudinal cross sectional view, and a radial cross sectional view of a first embodiment of a needle probe housing which defines one sample port therein, wherein the probe structure of FIG. 6 is part of the prior art.
Figure 7:
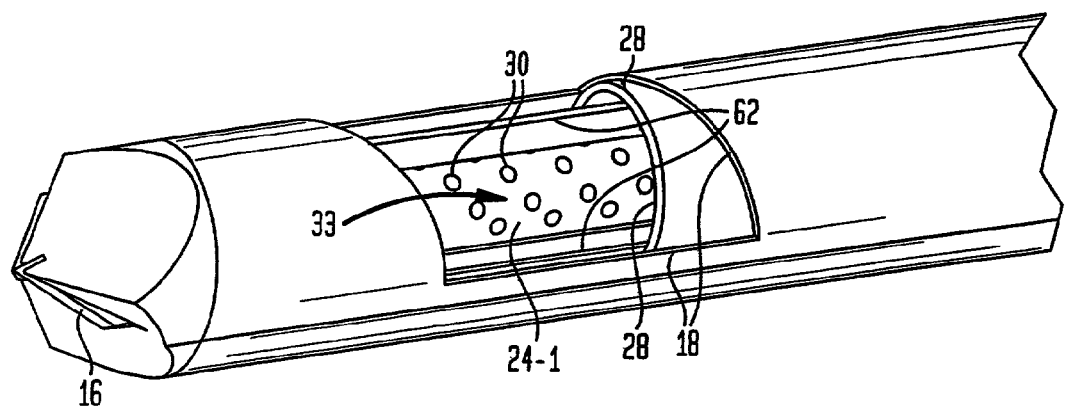
Figure 8:
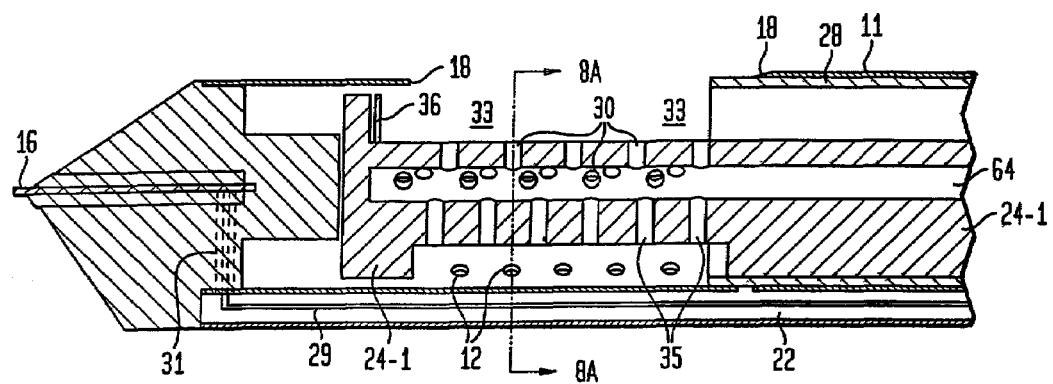
Figure 8A:
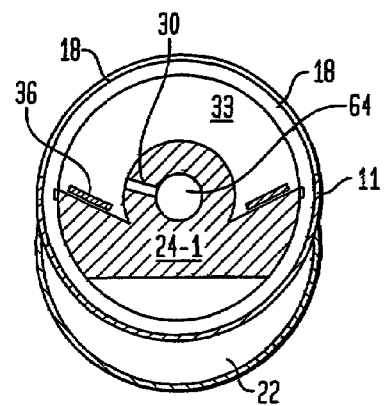

FIGS. 6, 7, 8 and 8A are respectively first and second perspective views, a longitudinal cross sectional view, and a radial cross sectional view of a first embodiment of a needle probe housing 11, which defines one sample port therein, wherein the probe structure of FIG. 6 is part of the prior art. FIGS. 7, 8 and 8A show the contribution thereto of a first embodiment of a perimeter shave insert 24-1 pursuant to the present invention.

FIG. 6 is a perspective view of just the distal end of the first embodiment of needle probe housing 11 with both the cutter 28 and the first embodiment of the perimeter shave insert 24-1 retracted therefrom, and illustrates an optional RF cutting/tunneling blade 16, vacuum openings 12 through the needle probe housing 11, and a single sample notch port 18 in the needle probe housing 11.

FIG. 7 is a perspective view of the distal end of the probe, and shows the cutter 28 and the first embodiment of a perimeter shave insert 24-1 positioned therein, having sidewalls 62, vacuum openings 30, and the specimen chamber 33, which are visible through the sample notch port 18 of the probe housing.

FIG. 8 is a longitudinal cross sectional view of the needle probe of FIG. 7 taken along its longitudinal axis, and illustrates a bottom vacuum lumen 22, and a cross sectional view of the first embodiment of the perimeter shave insert 24-1, with the specimen chamber 33 being aligned with the single sample notch port 18 and the cutter 28 being in a retracted proximal position, from which it is moved while rotating to an extended distal position to take a perimeter tissue slice 34. The perimeter shave insert 24-1 has a central, axially-extending vacuum port 64 communicating through the vacuum ports 30 with the specimen chamber 33 and communicating through vacuum ports 35 with the vacuum ports 12 of the housing. FIG. 8 also illustrates the tissue retraction arm 36, and an electrical wire 29 extending through the bottom vacuum lumen to the distal end of the probe where it extends through a radial aperture 31 to provide RF electrical signals to the RF cutting/tunneling tip 16.

FIG. 8A is an axial cross sectional view of the probe of FIG. 8 taken along sectional arrows 8A—8A in FIG. 8, and illustrates the specimen chamber 33, the bottom lumen 22, and the tissue retraction arm 36.

Figure 12:
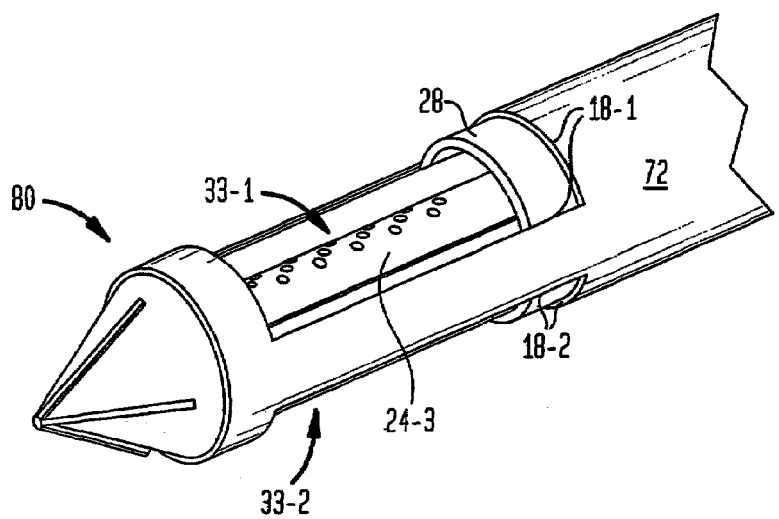
Figure 13:
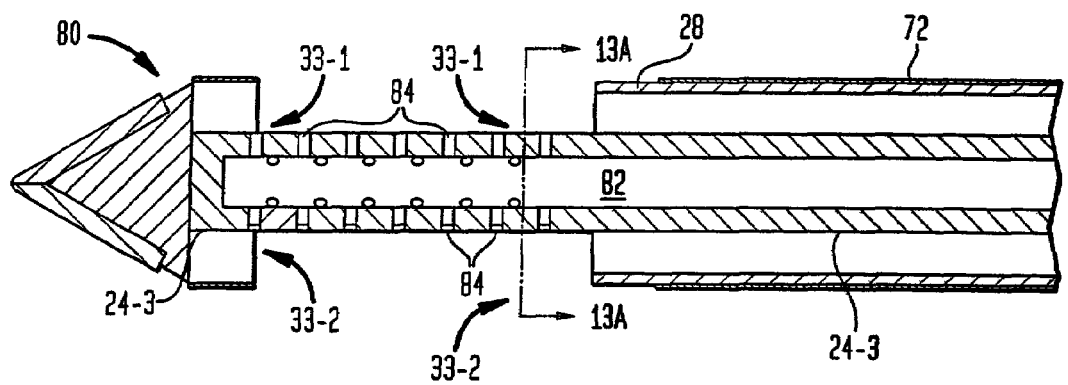

To reduce procedure time and possibly increase orientation accuracy, other embodiments of the probe, as illustrated by insert 24-3 in FIGS. 12 and 13, can include two sample ports oriented 180 degrees apart. The insert 24-2 has two relief features corresponding to the two probe ports. The advantages relative to a single-port shaver are a lower cost needle due to elimination of a vacuum lumen, and less procedural steps are involved because the surgeon obtains two shaves with each pass instead of just one.

The two-opening design may offer more control over how the vacuum displaces tissue during the shaving steps. Because the vacuum is pulling the tissue from opposite sides, a static tension is applied to the tissue 90 degrees offset from the bowls. The static tension reduces the possibility of the vacuum pulling tissue into the probe that is not directly in front of the sample notch. This improves the chances of cutting 360 degrees of contiguous tissue pieces so that the entire margin around the initial core is removed.

These embodiments rotate the needle only once during the procedure to obtain four perimeter tissue samples, such that there is less potential for the outside of the needle to displace tissue unpredictably, again ensuring that a complete margin is removed and that the orientation of the shaves is preserved for the pathologist.

FIGS. 9, 10, 11, and 11A are respectively first and second perspective views, a longitudinal cross sectional view, and an axial cross sectional view of a second embodiment 70 of a needle probe which defines two sample ports 18-1, 18-2. The two sample port probe 70 has a hollow cylindrical probe/needle body 72 which has RF electrodes 16 at its distal end.

Figure 9:
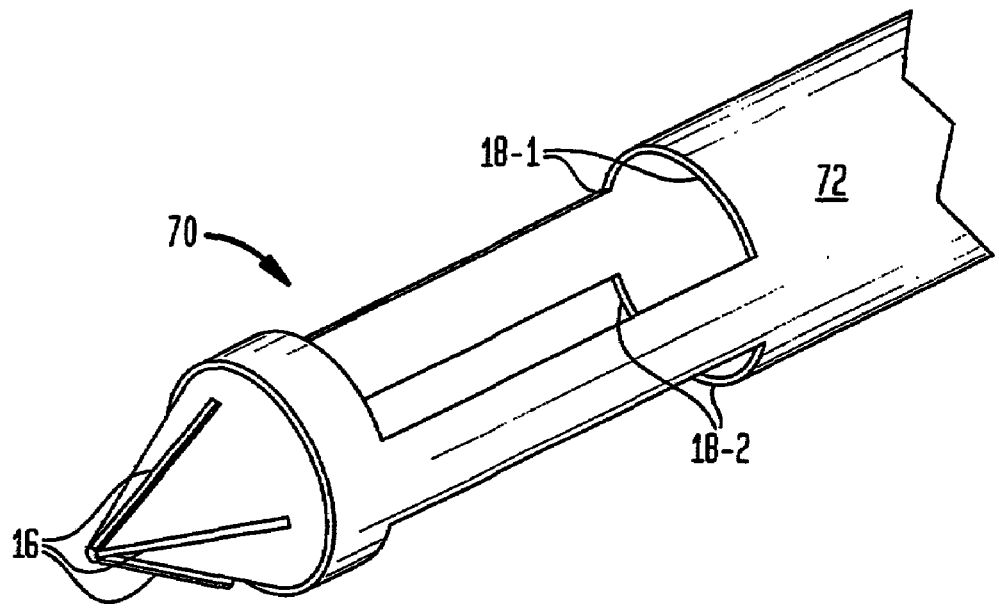
FIGS. 9, 10, 11, 11A and 12 are respectively first and second perspective views, a longitudinal cross sectional view, a radial cross sectional view, and third perspective view of a second embodiment of a needle probe housing which defines two sample ports.

FIG. 9 illustrates just the probe needle housing 72 having an RF cutting tip 16 and defining the two sample ports 18-1, 18-2.

Figure 10:
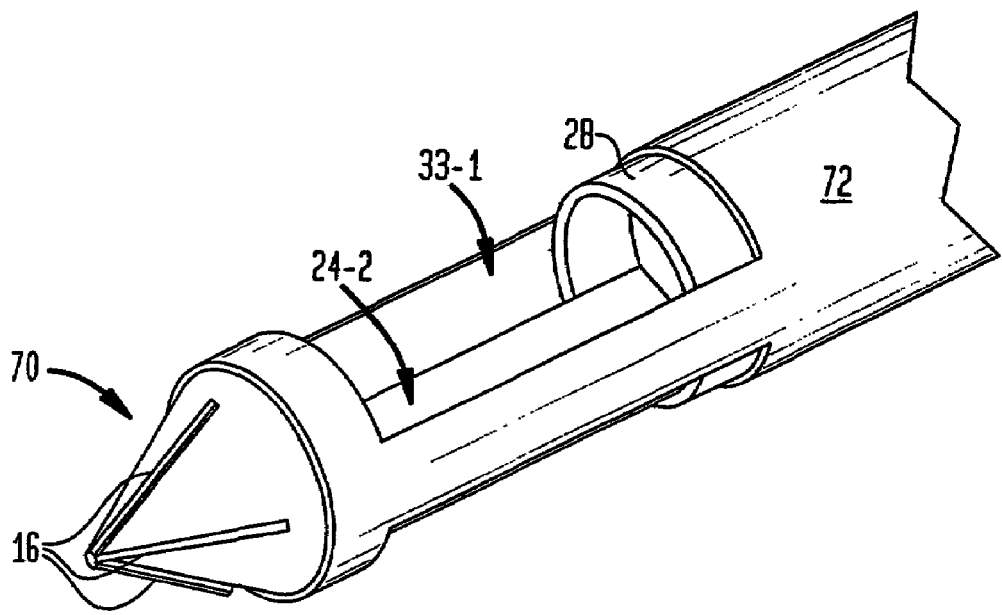

FIG. 10 illustrates the probe housing of FIG. 9 having a core insert 24-2 for the removal of a core tissue sample inserted therein, and also shows the cutter 28 shown in a partially retracted position.

Figure 11:
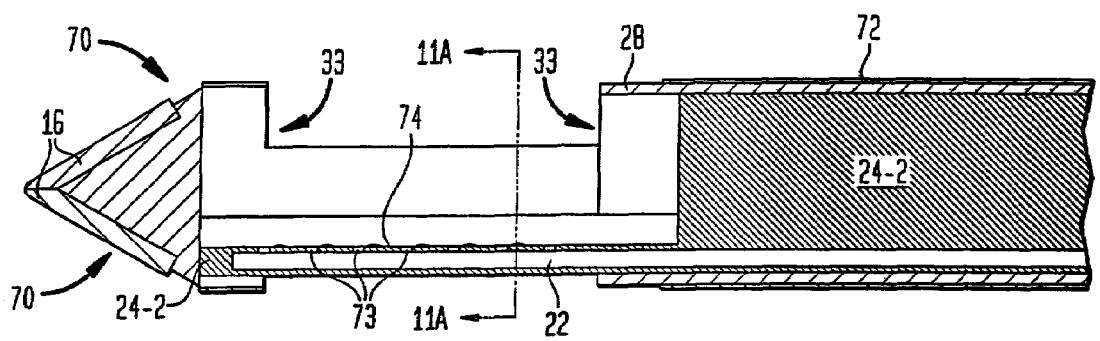
Figure 11A:
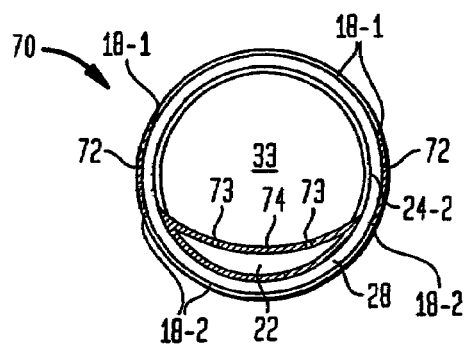

FIG. 11 is a longitudinal cross sectional view of the probe 70, and illustrates the core insert 24-2 having a vacuum lumen 22 defined in the lower portion of the insert, which communicates through vacuum ports 73 with the specimen chamber 33 through a partition 74 separating the specimen chamber 33 from the vacuum lumen 22. FIG. 11A is an axial cross sectional view further illustrating details of the probe and core insert of FIG. 11, including the core specimen chamber 33 and the vacuum lumen 22.

Figure 13A:
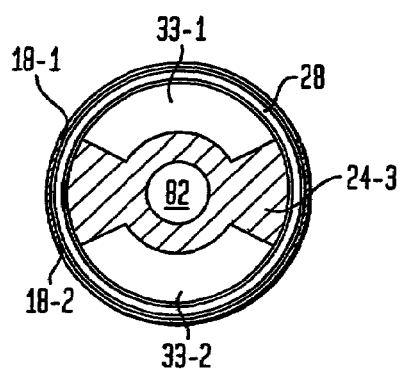

FIGS. 12, 13 and 13A are respectively a perspective view, a longitudinal cross sectional view, and a radial cross sectional view, taken along sectional arrows 13A—13A in FIG. 13, of the second embodiment of the needle probe 72 with two sample notch ports and further having a second embodiment of a perimeter shave insert 24-3 inserted therein to remove margin specimens of tissue after the core insert 24-2 has been used to remove an initial core tissue sample. The perimeter shave insert 24-3 has a central axially-extending vacuum lumen 82 which communicates through radially extending vacuum ports 84 with first and second radially-opposed and symmetrical specimen chambers 33-1, 33-2, such that two perimeter tissue specimens 34 can be taken at one time. One advantage of this embodiment is that the two vacuum forces on opposite sides of the probe counterbalance each other. The probe housing 72 and insert can then be rotated 90 degrees and the next two shaves of perimeter tissue can be taken through specimen chambers 33-1 and 33-2 of the probe housing. These four shaves provide a contiguous 360 degrees margin of tissue around the initial core tissue sample, as illustrated in FIG. 4.

Figure 14:
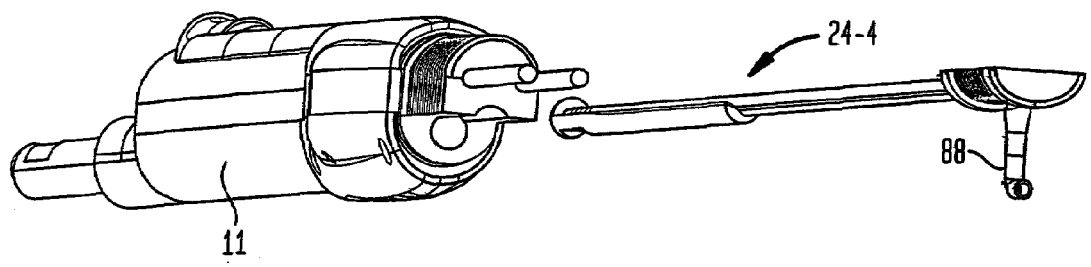
FIG. 14 is a perspective view of an embodiment of a perimeter cut biopsy probe pursuant the present invention wherein a perimeter shave insert is shown after its removal from the proximal end of a needle probe housing.

FIG. 14 is a perspective view of an embodiment of a perimeter cut biopsy probe pursuant the present invention wherein a perimeter shave insert 24-4, having a vacuum connection fitting 88, is shown after its removal from the proximal end of a needle probe housing 11. As illustrated broadly in FIG. 14, the perimeter shave insert is inserted and removed longitudinally through the proximal end of the needle probe housing. The core insert is inserted and removed longitudinally through the proximal end of the needle probe housing in a similar manner.

The present invention provides a perimeter cut biopsy probe which includes an insert to excise tissue surrounding a center core(s) of removed tissue. The additional tissue provides an effective evaluation of whether all the desired tissue has been excised and of whether an acceptable margin of healthy tissue has been removed.

Compared to today's typical lumpectomy procedure/technique (needle localization followed by a lumpectomy where a scissors, scalpel, or monopolar pencil is used to dissect the tissue), the perimeter cut biopsy probe of the present invention more efficiently removes tissue (i.e. removes only desired/required tissue) resulting in reduced breast dimpling or better cosmesis. It also reduces the length of the incision.

The perimeter cut biopsy probe of the present invention provides a lumpectomy device that is compatible with imaging systems involving breast compression/immobilization and stereotactic localization (e.g. Mammography, MRI, PET). The subject invention also reduces or eliminates steps in the care pathway of a lumpectomy procedure (e.g. eliminates wire localization procedure), and reduces the current re-excision rate which is (20–50%) resulting from inadequate margins.

The perimeter cut biopsy probe of the present invention improves the accuracy of processing and analysis of the lumpectomy specimen by pathology, and maintains or improves the ability of the surgeon to determine the orientation of the tissue as it was excised in the breast.

The perimeter cut biopsy device of the present invention employs conventional MAMMOTOME® features (vacuum assist, lateral sample bowl, rotating and translating circular cutter), as described for instance in U.S. Pat. Nos. 5,526,822, 5,769,086, 5,775,333, 5,980,469 and 6,086,544, which patents are incorporated herein by reference. An insert located within the cutter replaces the knock-out pin after the initial center core(s) of tissue is removed. The insert is designed to remove slices of tissue located at the perimeter of the initial cavity to aid in margin determinations. It utilizes vacuum to pull tissue into the bowl. The perimeter slices are removed individually similar to the current Mammotome® device.

Optional features allow multiple perimeter slices to be stacked within the probe/cutter as they are cut. To remove the stacked slices, the insert is removed from the probe. The order of excision and orientation of the slices is preserved. Also, by stacking the slices the overall procedure time is reduced. To orient the cylindrical center core(s), a portion of the core can be cauterized to record and preserve the rotational orientation of the core. The probe tip can be designed to facilitate tunneling and maneuvering of the probe, to result in reduced bleeding along the tunneling path. RF (monopolar or bipolar) and ultrasonic (e.g. Ultracision™) are two potential approaches. Holes or ports can be located in the probe and the cutter. When the cutter is at specific positions, these holes are aligned to allow fluid to be communicated from within the cutter to the outside perimeter of the probe. This allows, for example, epinephrine to be injected through the vacuum tubing into the probe and into the tissue surrounding the probe to manage bleeding.

Summary of Procedural Steps

Energy assistance (e.g. RF, ultrasonic) located at the probe tip is used to tunnel to the suspicious mass while using Ultrasound, X-Ray, MRI, or PET imaging. This could potentially occur without the aid of a needle localization wire. In the case of a mass, the intent is to tunnel along the outer edge of the mass, although the probe could also be inserted through the mass.

With the lesion adjacent to the sample bowl in the probe tip, large cylindrical core or cores of tissue are taken, similar to the current biopsy procedure. Based on a gross examination of the large tissue core, if it is believed that a majority of the lesion has been removed, the probe is left in place, and the knock-out pin is replaced with a shaving insert. Based on imaging or gross examination, if it is believed that a large portion of the mass remains in the breast, another large core of tissue could be removed.

With the shaving insert inserted into the probe, a series of perimeter slices of tissue are dissected as the probe is rotated about its longitudinal axis. The perimeter slices are sequentially stacked within the probe. When a sufficient number of perimeter slices has been dissected, the insert subassembly is removed from the probe, to allow the perimeter slices to be removed from the insert subassembly. Based on imaging or gross examination of the perimeter slices, it is possible to remove tissue beyond the initial 360 degree sampling pass.

With the tissue removed from the body, the core tissue and the perimeter slices can be reoriented with respect to each other and to the cavity for inspection and analysis by the surgeon, radiologist and/or pathologist. The perimeter slices are preferably intended to fit into a conventional permanent-sectioning cassette utilized in pathology. Based on real-time palpation, visualization, and other means (e.g. frozen sections, X-Ray, optical diagnostic scanning devices, etc.), additional tissue can be excised in a specific area of the cavity based on the real-time evaluation of the excised tissue and the specific orientation of the specimen.

An alternate embodiment can be used to acquire a single piece margin specimen, in which a non-cylindrical, non-rotating cutter can be utilized. The device employs a similar insert, however, an arcuate cutter cuts a portion of the circumference while advancing. Sequentially, the device is rotated and the cutter severs the next portion of the tissue margin. Once the device has been rotated around the entire circumference, a single piece margin is obtained. The cutting mechanism for this device also preferably employs an energy source (e.g. RF, ultrasonic, etc.).

A preferred embodiment of the present invention includes an RF (mono or bipolar) probe tip to aid tunneling and fine positioning of the probe with respect to the tissue/lesion. An RF probe tip should theoretically allow a blunter probe to improve access near the chest wall, and to cauterize tissue (i.e. reduce bleeding) while tunneling. An alternative embodiment can incorporate a passive sharp metal tip in a razor blade type of design. The cylindrical center core(s) is preferably marked as by cauterizing/branding, as shown in FIG. 1, to orient it relative to the perimeter slices and the tissue cavity. A port can be provided on the external surface of the needle probe to allow a vacuum or epinephrine to be applied to tissue surrounding the probe to manage bleeding. The perimeter slice thickness, width, and length are designed to fit into a standard cassette used for permanent sectioning during pathological evaluation.

While several embodiments and variations of the present invention for a perimeter cut biopsy probe are described in detail herein, it should be apparent that the disclosure and teachings of the present invention will suggest many alternative designs to those skilled in the art.

What is claimed is:

1. A method for obtaining a biopsy sample, the method comprising the steps of:

positioning a hollow biopsy probe having at least two sample ports in a tissue mass of a patient;

disposing a first insert in the probe to obtain a core tissue sample;

displacing a core specimen of tissue into the probe by displacing the core specimen through at least one sample port in the probe;

axially translating a cutter within die hollow biopsy probe to sever the core specimen of tissue from the tissue mass;

removing the core tissue specimen from the probe;

disposing a second insert within the probe to obtain a perimeter tissue sample, wherein the insert at least partially defines at least one specimen chamber;

rotating the insert to align a specimen chamber with one of the sample ports;

displacing a perimeter tissue specimen from the tissue mass into a specimen chamber through a sample port in the probe; and axially translating the cutter to sever the perimeter specimen from the tissue mass.

2. The method of claim 1 further comprising communicating a vacuum source with the specimen chamber.

3. The method of claim 1 further comprising marking a perimeter tissue specimen to preserve the orientation of the specimen of tissue.

4. The method of claim 1 wherein at least one of the first and second inserts provides two specimen chambers, and wherein the method comprises the step of rotating the insert to align the two specimen chambers with two sample ports.

5. The method of claim 1 wherein the probe comprises multiple sample ports and wherein at least one of the first and second inserts defines multiple specimen chambers, and wherein the method comprises aligning at least two specimen chambers with two sample ports to obtain first and second perimeter tissue specimens simultaneously.

6. The method of claim 1 comprising severing a plurality of perimeter tissue specimens.

7. The method of claim 6 further comprising stacking perimeter tissue specimens in a position proximal to the specimen chamber.

8. A method for obtaining a biopsy sample, the method comprising the steps of:

providing a biopsy probe;

providing a core insert adapted for obtaining a core tissue sample;

providing a perimeter insert adapted for obtaining a perimeter tissue sample;

positioning the biopsy probe within a tissue mass;

positioning the core insert in the biopsy probe;

displacing a core specimen of tissue into the probe;

severing at least a portion of the core specimen to provide a core tissue sample;

removing the core insert from the probe;

inserting the perimeter insert in the biopsy probe after the step of removing the core insert and without removing the biopsy probe from the tissue mass;

displacing a perimeter specimen of tissue into the probe; and severing at least a portion of the perimeter speciment to provide a perimeter tissue sample.

9. The method of claim 8 comprising displacing tissue into the probe using vacuum.

10. The method of claim 8 comprising severing a plurality of perimeter tissue specimens.

11. The method of claim 8 further comprising stacking perimeter tissue specimens.

12. The method of claim 8 further comprising marking a perimeter tissue specimen to preserve the orientation of the specimen of tissue.

13. The method of claim 8 wherein at least one of the inserts comprises at least two specimen chambers.

14. The method of claim 8 wherein the probe comprises multiple sample ports and wherein at least one insert defines multiple specimen chambers.

* * * * *